United States Patent [19]

Angst et al.

[11] Patent Number: 5,925,367

[45] Date of Patent: *Jul. 20, 1999

[54] PEST CONTROL WITH UV BLOCKERS AND PHEROMONES

[75] Inventors: Max Angst, Magden; François Gugumus, Allschwil; Günther Rist, Arlesheim, all of Switzerland; Manfred Vogt, Wallbach, Germany; Jean Rody, Riehen, Switzerland

[73] Assignee: Ciba-Geigy Corporation, Summit, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/376,132

[22] Filed: Jan. 19, 1995

Related U.S. Application Data

[63] Continuation of application No. 08/240,302, May 9, 1994, abandoned, which is a continuation of application No. 08/097,865, Jul. 26, 1993, abandoned, which is a continuation of application No. 07/825,681, Jan. 27, 1992, abandoned, which is a continuation of application No. 07/453,633, Dec. 20, 1989, abandoned.

[30] Foreign Application Priority Data

Dec. 28, 1988 [CH] Switzerland .............................. 4825/88

[51] Int. Cl.⁶ .................................................. A01N 25/22
[52] U.S. Cl. .......................... 424/405; 424/406; 424/407; 424/417; 424/421; 514/360; 514/513; 514/613; 514/972
[58] Field of Search .................................... 424/405–417, 424/421, 484–489, 43, 45, 84; 514/360, 513, 613, 972

[56] References Cited

U.S. PATENT DOCUMENTS 4,666,747  5/1987  Quinn ...................................... 427/421
4,732,762  3/1988  Sjorgren ................................. 424/409
4,855,133  8/1989  Kamei et al. .
4,954,497  9/1990  Kamikado et al. .................. 514/235.5

FOREIGN PATENT DOCUMENTS 0055475   11/1985   European Pat. Off. .
62-26208   2/1987   Japan .
1548920    7/1979   United Kingdom .
2063068    6/1981   United Kingdom .
2064323    6/1981   United Kingdom .
2141932    1/1985   United Kingdom .
2141932   10/1987   United Kingdom .

OTHER PUBLICATIONS

Yamamoto et al., "Pesticide Design—Strategy and Tactics," Soft Science Inc. (1979), pp. 1039–1050.

*Primary Examiner*—Neil S. Levy
*Attorney, Agent, or Firm*—Marla J. Mathias; William A. Teoli, Jr.; John D. Peabody, III

[57] ABSTRACT

A composition for controlling harmful insects and representatives of the order Acarina, containing as biologically active components a) a substance that modifies the behavior of the pests and b) at least one pesticidally active compound, wherein the biologically active components are contained in a flowable or viscous non-hardening matrix that is resistant to water and weather, is protected against light and is suitable for distribution in the form of droplets or droplet-like units or spots that adhere to a substrate, by means of which matrix the behavior-modifying substance is protected against UV radiation and from which it is slowly released in a biologically effective amount over a prolonged period, and wherein the pesticidally active compound can be taken up in a pesticidally effective amount from the surface of the droplets or droplet-like units or spots by the pests to be controlled; as well as a method of controlling the said pests, especially plant-destructive insects.

8 Claims, No Drawings

PEST CONTROL WITH UV BLOCKERS AND PHEROMONES

This a continuation of Ser. No. 08/240,302 filed May 9, 1994, now abandoned, which is a continuation of Ser. No. 08/097,865 filed Jul. 26, 1993 now abandoned which is a continuation of Ser. No. 07/825,681 filed Jan. 27, 1992 now abandoned which is a continuation of Ser. No. 07/453,633 filed Dec. 20, 1989 now abandoned.

The present invention relates to a novel pesticidal composition for controlling harmful insects and representatives of the order Acarina, especially those of the plant-destructive kind, wherein a substance that alters the behaviour of the pests is freed in a biologically effective amount.

In the control of plant pests, especially insects and spider mites, in agricultural crops, especially monocrops, the aim in general is to allow as little contact as possible of the pesticidal active ingredients with the crop plants to be protected and the locus thereof, and with the soil in which they are growing. The pests found mostly on the plants should themselves, however, be exposed as much as possible to the active ingredient, whether by contact action, stomach poison action or gaseous phase action. A further aim is to ensure that useful insects and warm-blooded animals are not significantly harmed by the pesticidal active ingredients. In order to achieve these aims, in accordance with the invention a composition and a method of control have been proposed with which, in principle, the behaviour of the pests to be controlled can be so specifically directed or selectively modified using signal substances that the pests are led to a source of pesticidal active ingredient that is provided in discrete regions within the crop area to be protected.

Of the behaviour-modifying substances, so far mainly pheromones have been used in practice, in traps, for the early recognition of pest attack, for controlling pest populations by interrupting or interfering with the normal pairing process, or for catching pests, mainly insects (cf. for example, GB-PS 1 548 920 and GB Patent Application 2 063 068). In general, behaviour-modifying substances, especially pheromones, must have a slow release over a relatively long period of time and need to be protected from the influences of light and weather. GB Patent Application 2 064 323, for example, describes sprayable, film-forming compositions containing UV stabilisers and antioxidants that are said to provide slow release of pheromones and be suitable for the control of insects (cf. also EP-PS 55 475). It is also known from PCT Application PCT/US 87/00243, for the control of spider mites, to spray a slow release substance that modifies the behaviour of pests onto the leaves of the plants to be treated, which substance is applied in combination with a miticide in the conventional form of a spray mixture. The distribution of flowable, copolymeric pheromone-containing insecticidal compositions in the form of limited regions in the form or droplets or spots that provide slow release of the pheromone is described in GB-PS 2 141 932. These copolymeric compositions can be applied to the leaves of plants to be protected in the form of thin films or droplets that harden or set.

It is not possible, however, to achieve the aims of the invention set forth at the beginning using the above-described compositions and methods of application, either because with the known pesticide/attractant combinations the entire agricultural area to be protected has to be given a surface cover spray, or because the compositions applied in discrete regions do not release the behaviour-modifying substances for a sufficient length of time or do not ensure adequate efficiency in respect of actual kill of the pests using a pesticidal active ingredient. In addition, the known formulations, which can be applied in droplet form (cf. GB-PS 2 141 932), do not meet requirements in practice as regards UV protection even though they contain UV absorbers, antioxidants etc. It has also been found that phytotoxic phenomena often occur using known compositions of this kind having a polymer-based formulation.

The disadvantages mentioned above have now been overcome by the compositions and methods of control according to the invention. The invention accordingly relates to a composition for controlling harmful insects and representatives of the order Acarina, containing as biologically active components a) a substance that modifies the behaviour of the pests and b) at least one pesticidally active compound, wherein this composition contains the biologically active components in a flowable or viscous non-hardening matrix that is resistant to water and weather, is protected against light and is suitable for distribution in the form of droplets or droplet-like units or spots that adhere to a substrate, by means of which matrix the behaviour-modifying substance is protected against UV radiation and from which it is slowly released in a biologically effective amount over a prolonged period, and the pesticidally active compound can be taken up in a pesticidally effective amount from the surface of the droplets or droplet-like units or spots by the pests to be controlled. The invention further relates to a method of controlling harmful, especially plant-destructive, insects and representatives of the order Acarina, which comprises applying to or distributing over the area to be protected against pest attack, or the crop area, the afore-described composition in the form of a predetermined number of discrete droplets or droplet-like units or spots, the behaviour-modifying substance being slowly released in a biologically effective amount over a prolonged period into the surrounding atmosphere.

It was surprisingly found that the composition of the invention is outstandingly suitable for pest control and at the same time has a good lasting action, is tolerated by plants and provides a high degree of preservation of useful insects. As a result of the use of the mentioned signal substances or attractants, the amount of insecticides, which are often toxic to warm-blooded animals and useful insects, required for the treatment of the crop areas to be protected can be restricted considerably. This novel procedure which is also advantageous from the ecological point of view belongs to those concepts that are based on integrated plant protection and have already received considerable attention. As mentioned, the formulations of the invention are distinguished especially by the fact that both the behaviour-modifying substance and the pesticidally active compound are present directly in a liquid or flowable UV absorbent. As a result, optimum and prolonged UV protection, especially of the sensitive behaviour-modifying substance, is achieved.

The compositions of the invention exhibit particular activity especially in the control of plant-attacking insects and representatives of the order Acarina. The compositions and methods of the invention are suitable especially for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and representatives of the order Acarina of the families: Ixodidae, Argasidae, Tetranychidae and Dermanyssidae.

The compositions of the invention are used preferably for controlling destructive phytophagous insects in forests, in plantations of ornamental and useful plants, especially in cotton crops (e.g. *Pectinophora gossypiella, Spodoptera*

*littoralis, Anthonomus grandis* and *Heliothis virescens*), in maize crops, in forestry and in viniculture. The compositions are distinguished by a pronounced activity not only against adult insects but also against larvae, especially of phytophagous insect pests.

The compositions of the invention can also be used for controlling flies, e.g. *Musca domestica* and *Stomoxys calcitrans*, mosquitos, and undesired populations of other insects, e.g. *Blatella germanica*, as well as for controlling ectoparasitic insects, e.g. *Lucilia sericata*, that harm domestic animals and livestock, for example by treating livestock buildings and pastures.

The following species of insects, for example, can be controlled successfully with the composition of the invention:

Acleris spp.
*Adoxophyes fasciata*
*Adoxophyes orana*
*Aegeria apiformis*
Agriotes spp.
*Agrotis ipsilon*
*Agrotis segetum*
*Amylois transitella*
*Anthonomus grandis*
*Aonidiella aurantii*
*Aonidiella citriana*
Archips spp.
Argyrotaenia spp.
Autographa spp.
*Blattella germanica*
*Busseola fusca*
*Cadra cautella*
*Chilo partellus*
*Chilo suppressalis*
*Choristoneura fumiferana*
*Choristoneura murinana*
*Choristoneura rosaceana*
Choristoneura spp.
Cnephasia spp.
Cochylis spp.
*Coleophora laricella*
Coleophora spp.
*Cossus cossus*
*Crocidolomia binotalis*
*Curculio caryae*
*Cydia pomonella*
*Dacus dorsalis*
*Dacus oleae*
Dacus spp.
Dasychira spp.
*Dendroctonus brevicomis*
*Dendroctonus frontalis*
*Dendroctonus ponderosae*
*Dendrolimus pini*
Dentroctonus spp.
Dermestes spp.
*Diabrotica balteata*
*Diabrotica longicornis*
*Diabrotica vigifera*
*Diabrotica barberi*
*Diabrotica undecimpunctata*
*Diatraea grandiosella*
*Diatraea saccharalis*
*Earias biplaga*
*Earias insulana*
*Earias vittella*
*Ephestia elutella*
*Ephestia kuehniella*
*Eucosma ponderosa*
*Eucosma sonomana*
Eucosma spp.
*Eupoecilia ambiguella*
*Euproctis similis xanthocampa*
Euxoa spp.
*Glossina morsitans morsitans*
Gnathotrichus spp.
*Grapholita funebrana*
*Grapholita janthinana*
*Grapholita molesta*
*Grapholita prunivora*
Grapholita sp.
*Hedya nubiferana*
*Heliothis armigera*
Heliothis spp.
*Heliothis virescens*
*Heliothis zea*
*Hylobius abietis*
*Hylotrupes bajulus*
*Ips paraconfusus*
Ips spp.
*Ips typographus*
*Keiferia lycopersicella*
*Leptinotarsa decemlineata*
*Leucoptera scitella*
*Lobesia botrana*
*Lymantria dispar*
*Lymantria monacha*
*Lyonetia clerkella*
Malacosoma spp.
*Mamestra brassicae*
*Manduca sexta*
*Musca domestica*
*Neodiprion sertifer*
Neodiprion spp.
*Operophtera brumata*
*Ostrinia nubilalis*
*Pammene rhediella*
Pammene spp.
Pandemis spp.
*Pandemis heparana*
*Panolis flammea*
*Pectinophora gossypiella*
Pectinophora spp.
*Periplaneta americana*
*Pityogenes chalcographus*
Pityokteines spp.
*Planococcus citri*
*Platypus flavicoruis*
*Plutella xylostella*
*Popillia japonica*
*Prays citri*
*Prays oleae*
*Pseudaulacaspis pentagona*
*Pseudococcus comstocki*
*Quadraspidiotus perniciosus*
*Scolytus multistriatus*
*Scolytus scolytus*
Scolytus spp.
Sesamia spp.
Sitotroga spp.
*Sparganothis pilleriana*
Sparganothis spp.
*Spodoptera exempta*
*Spodoptera exigua*

Spotoptera frugiperda
Spotoptera littoralis
Spotoptera litura
Spotoptera spp.
*Stomoxys calcitrans*
*Synanthedon formicaeformis*
Synanthedon spp.
*Tetranychus urticae*
*Thaumetopoea pityocampa*
*Tortrix viridana*
*Trichoplusia ni*
*Trogoderma granarium*
Trogoderma spp.
*Trypodendron domesticum*
*Trypodendron lineatum*
Vespula spp.
Yponomeuta spp.
*Zeiraphera diniana*
*Zeuzera pyrina*

The compositions of the invention also exhibit good activity against plant-destructive acarids (spider mites: e.g. of the Tetranychidae, Tarsonemidae, Eriophydae, Tyroglyphidae and Glycyphagidae families). The compositions of the invention are suitable especially for controlling the following species of mites that attack fruit and vegetable crops: *Tetranychus urticae, Tetranychus cinnabarinus, Panonychus ulmi, Bryobia rubrioculus, Panonychus citri, Eriophyes pyri, Eriophes ribis, Eriophyes vitis, Tarsomemus pallidus, Phyllocoptes vitis* and *Phyllocoptura oleivora*.

The good pesticidal activity of the compositions of the invention corresponds to a killing rate (mortality) of at least 50–60% of the mentioned pests.

Behaviour-modifying substances suitable for the invention are chiefly pheromones, but kairomones and attractants are also suitable. Such signal substances are effective even in extraordinarily low concentrations and can modify the behaviour of insects in a manner that renders possible their control. The proportion of behaviour-modifying substance in the compositions of the invention is preferably from 0.01 to 30% by weight. In the case of pheromones, the proportions used are preferably from 0.01 to 2.0% by weight, and in the case of kairomones and attractants, which are usually contained in compositions for controlling larval stages, the proportions used are from 0.5 to 30% by weight. Pheromones are sexual signal substances, produced in most cases by the adult females of pests, mainly insects, that attract individuals of the opposite sex of the same pest species. The natural pheromones and pheromone mixtures are volatile and their attracting effect can reach over long distances. In principle, all pheromones described in the literature are suitable for the purposes of the invention. The structure and composition of pheromones is known from the literature, c.f., e.g.: A. F. Kydoneus et al., "Insect Suppression with Controlled Release Pheromone Systems", CRC Press (1982); H. Arn et al., "List of Pheromones of Lepidoptera and Related Attractants", OILB (1986).

The following pheromones, for example, may be used within the scope of the present invention:

Z-5-Decenyl acetate
Dodecanyl acetate
Z-7-Dodecenyl acetate
E-7-Dodecenyl acetate
Z-8-Dodecenyl acetate
E-8-Dodecenyl acetate
Z-9-Dodecenyl acetate
E-9-Dodecenyl acetate
E-10-Dodecenyl acetate
11-Dodecenyl acetate
Z-9,11-Dodecadienyl acetate
E-9,11-Dodecadienyl acetate
Z-11-Tridecenyl acetate
E-11-Tridecenyl acetate
Tetradecanyl acetate
E-7-Tetradecenyl acetate
Z-8-Tetradecenyl acetate
E-8-Tetradecenyl acetate
Z-9-Tetradecenyl acetate
E-9-Tetradecenyl acetate
Z-10-Tetradecenyl acetate
E-10-Tetradecenyl acetate
Z-11-Tetradecenyl acetate
E-11-Tetradecenyl acetate
Z-12-Pentadecenyl acetate
E-12-Pentadecenyl acetate
Hexadecanyl acetate
Z-7-Hexadecenyl acetate
Z-11-Hexadecenyl acetate
E-11-Hexadecenyl acetate
Octadecanyl acetate
E,Z-7,9-Dodecadienyl acetate
Z,E-7,9-Dodecadienyl acetate
E,E-7,9-Dodecadienyl acetate
Z,Z-7,9-Dodecadienyl acetate
E,E-8,10-Dodecadienyl acetate
E,Z-9,12-Dodecadienyl acetate
E,Z-4,7-Tridecadienyl acetate
4-methoxy-cinnamaldehyde
β-Ionone
Estragol
Eugenol
Indole
8-Methyl-2-decyl-propanoate
E,E-9,11-Tetradecadienyl acetate
Z,Z-9,12-Tetradecadienyl acetate
Z,Z-7,11-Hexadecadienyl acetate
E,Z-7,11-Hexadecadienyl acetate
Z,E-7,11-Hexadecadienyl acetate
E,E-7,11-Hexadecadienyl acetate
Z,E-3,13-Octadecadienyl acetate
E,Z-3,13-Octadecadienyl acetate
E,E-3,13-Octadecadienyl acetate
Ethanol
Hexanol
Heptanol
Octanol
Decanol
Z-6-Nonenol
E-6-Nonenol
Dodecanol
11-Dedecenol
Z-7-Dedecenol
E-7-Dedecenol
Z-8-Dedecenol
E-8-Dedecenol
E-9-Dedecenol
Z-9-Dedecenol
E-9,11-Dodecadienol
Z-9,11-Dodecadienol
Z,E-5,7-Dodecadienol
E,E-5,7-Dodecadienol
E,E-8,10-Dodecadienol
E,Z-8,10-Dodecadienol
Z,Z-8,10-Dodecadienol
Z,E-8,10-Dodecadienol E,Z-7,9-Dodecadienol
Z,Z-7 9-Dodecadienol
E-5-Tetradecenol
Z-8-Tetradecenol
Z-9-Tetradecenol
E-9-Tetradecenol
Z-10-Tetradecenol
Z-11-Tetradecenol
E-11-Tetradecenol
Z-11-Hexadecenol
Z,E-9,11-Tetradecadienol
Z,E-9,12-Tetradecadienol
Z,Z-9,12-Tetradecadienol
Z,Z-10,12-Tetradecadienol
Z,Z-7,11-Hexadecadienol
Z,E-7,11-Hexadecadienol
(E)-14-Methyl-8-Hexadecen-1-ol
(Z)-14-Methyl-8-Hexadecen-1-ol
E,E-10,12-Hexadecadienol
E,Z-10,12-Hexadecadienol
Dodecanal
Z-9-Dodecenal
tetradecanal
Z-7-Tetradecenal
Z-9-Tetradecenal
Z-11-Tetradecenal
E-11-Tetradecenal
E-11,13-Tetradecadienal
E,E-8,10-Tetradecadienal
Z,E-9,11-Tetradecadienal
Z,E-9,12-Tetradecadienal
Hexadecanal
Z-8-Hexadecenal
Z-9-Hexadecenal
Z-10-Hexadecenal
E-10-Hexadecenal
Z-11-Hexadecenal
E-11-Hexadecenal
Z-12-Hexadecenal
Z-13-Hexadecenal
(Z)-14-Methyl-8-Hexadecenal
(E)-14-Methyl-8-Hexadecenal
Z,Z-7,11-Hexadecadienal
Z,E-7,11-Hexadecadienal
Z,E-9,11-Hexadecadienal
E,E-10,12-Hexadecadienal
E,Z-10,12-Hexadecadienal
Z,E-10,12-Hexadecadienal
Z,Z-10,12-Hexadecadienal
Z,Z-11,13-Hexadecadienal
Octadecanal
Z-11-Octadecenal
E-13-Octadecenal
Z-13-Octadecenal
Z-5-Decenyl-3-methyl-butanoate

| | |
|---|---|
| Disparlure | (+) cis-7,8-Epoxy-2-methyloctadecane |
| Seudenol | 3-Methyl-2-cyclohexhexen-1-ol |
| Sulcatol | 6-Methyl-5-bepten-2-ol |
| Ipsenol | 2-Methyl-6-methylene-7-octen-4-ol |
| Ipsdienol | 2-Methyl-6-methylene-2,7-octadien-4-ol |
| Grandlure I | cis-2-Isopropenyl-1-methylcyclobutane ethanol |
| Grandlure II | Z-3,3,-Dimethyl-1-cyclohexane ethanol |
| Grandlure III | Z-3,3,-Dimethyl-1-cyclohexane acetaldehyde |
| Grandlure IV | E-3,3,-Dimethyl-1-cyclohexane acetaldehyde |
| cis-2-Verbenol | cis-4,6,6-Trimethylbicyclo[3.1.1]hept-3-en-2-ol |
| | cucurbitacin |
| | 2-Methyl-3-buten-2-ol |
| | 4-Methyl-3-heptanol |
| Cucurbitacin | |
| 2-Methyl-3-buten-2-ol | |
| 4-Methyl-3-heptanol | |
| α-Pinen | 2,6,6-Trimethylbicyclo[3.1.1]hept-2-ene |
| α-Caryophyllen | 4,11,11-Trimethyl-8-methylenebicyclo[7.2.0] undecane Z-9-Tricosene |
| α-Multistriatin | 2(2-endo,4-endo)-5-Ethyl-2,4-dimethyl-6,8-dioxabicyclo-[3.2.1]octane |
| Methyleugenol | 1,2-Dimethoxy-4-(2-propenyl)phenol |
| Lineatin | 3,3,7-Trimethyl-2,9-dioxatricyclo[3.3.1.0]nonane |
| Cbalcogran | 2-Ethyl-1,6-dioxaspiro[4.4]nonane |
| Frontalin | 1,5-Dimethyl-6,8-dioxabicyclo[3.2.1]octan |
| endo-Brevicomin | endo-7-Ethyl-5-methyl-6,8-dioxabicyclo[3.2.1]octane |
| exo-Brevicomin | exo-7-Ethyl-5-methyl-6,8-dioxabicyclo[3.2.1]octane |
| | (Z)-5-(1-Decenyl)dihydro-2(3H)-furanone |
| Farnesol | 3,7-,11-Trimethyl-2,6,10-dodecatrien-1-ol |
| Nerolidol | 3,7-,11-Trimethyl-1,6,10-dodecatrien-3-ol |
| | 3-Methyl-6-(1-methylethenyl)-9-decen-1-ol-acetate |
| | (Z)-3-Methyl-6-(1-methylethenyl)-3,9-decadien-1-ol-acetate |
| | (E)-3,9-Methyl-6-(1-methylethenyl)-5,8-decadien-1-ol-acetate |
| | 3-Methylene-7-methyl-octen-1-ol-propionate |
| | (Z)-3,7-Dimethyl-2,7-octadien-1-ol-propionate |
| | (Z)-3,9-Dimethyl-6-(1-methylethenyl)-3,9-decadien-1-ol-propionate |

Kairomones, too, are signal substances of natural origin. They are produced by plants and consist chiefly of a mixture of a number of different volatile odorous substances. Kairomones are able to attract insects and representatives of the order Acarina. Depending on the concentration, however, they may also have a repelling effect. The activity of kairomones should be seen in conjunction with the fact that insects and acarines form a close living partnership with the relevant plants. Kairomones suitable for the purposes of the invention and methods of obtaining them are described, for example, in the following literature sources: Science, 154, 1392–93 (1966); P. A. Hedin "Bioregulators for Pest Control", American Chemical Society, Washington, 353–366 (1985).

So-called "attractants" are known chemical compounds that are relatively readily available and can exert behaviour-modifying effects on pests for the purposes of making these pests accessible and permitting substantial exposure thereof to the action of pesticides that are simultaneously present. Such attractants, which can also be used for the purposes of the invention, preferably in combination with pheromones and/or kairomones, are known, for example, from the following literature sources: G. R. Waller, "Allelochemicals: Role in Agriculture and Forestry", ACS, Washington, 431–438 (1987); Entomol. exp. appl. 41, 11–16 (1986); Can. Entomol. 115, 1–5 (1983).

In a specific embodiment of the invention, the matrix contains the behaviour-modifying substance in microencapsulated form. For this, the behaviour-modifying substance is encapsulated in a manner known per se in suitable polymers or mixed polymers of synthetic or natural origin, and can be released through the walls of the microcapsules slowly or in a controlled manner. By selection of the kind of encapsulation, especially the kind of polymeric encapsulating material, and also of the capsule wall strength and capsule size, it is possible to adapt the duration of the release of the behaviour-modifying substance to the particular requirements of agricultural practice.

In a further embodiment of the invention, the behaviour-modifying substance can also be incorporated into a granulate that is capable of releasing it slowly and in a controlled manner. Like the above-mentioned microcapsules, the granulate is present in the matrix and is distributed together with the other active ingredients proposed in accordance with the invention in the form of droplets or droplet-like units. The granulates may consist of small-particled inorganic carriers and/or organic polymers such as those familiar to the person skilled in the art.

Conventional insecticidal and acaricidal active ingredients that are suitable and are known for controlling the relevant pests are used as pesticidally active compounds in the compositions and preparations of the invention. Obviously, the pesticidal active ingredients must be compatible with the other constituents of the flowable or viscous composition of the invention and must be at least substantially soluble therein. For this reason preference is given in accordance with the invention to liquid pesticidally active compounds. However, the pesticidal active ingredients must not evaporate too quickly, but should be present at or on the surface of the applied droplets or droplet-like units or spots for a reasonable period of time so as to render possible the uptake of the active ingredient by the pest to be controlled. Accordingly, preferably pesticidal contact-active ingredients are present in the compositions of the invention. The compositions according to the invention generally contain from 0.1 to 10% by weight, preferably from 1 to 5% by weight, of the pesticidally active compound. Representatives of the following classes of pesticidal active ingredient are suitable for the purposes of the invention: carbamates, organophosphorus compounds, nitrophenols and derivatives thereof, formamidines, ureas, phenylbepyrethreas, pyrethroids, chlorinated hydrocarbons and Bacillus thuringiensis preparations.

Preferably, the compositions of the invention contain as classes of pesticidally active compounds carbamates, organophosphorus compounds, pyrethroids and insect-growth regulators.

Suitable carbamates are, for example:

| | |
|---|---|
| CLOETOCARB | BENDIOCARB |
| BPMC | CARBOFURAN |
| METHOMYL | CARBOSULFAN |
| BUFENCARB | PIRIMICARB |
| DIOXACARB | ISOPROCARB |
| THIODICARB | BENFURACARB |
| FURATHIOCARB | ALDICARB |
| NITRILACARB | CARBARYL |
| METHOMYL | THIODICARB |
| OXAMYL | |

Suitable organophosphorus compounds are, for example:

| | | |
|---|---|---|
| DIMETHOAT | PROFENOFOS | MALATHION |
| ZOLAPROFOS | AZAMETHIPHOS | CHLORPYRIFOS |
| AZINPHOS-METHYL | METHACRIFOS | CHLORPYRIFOS-M |
| SULPROFOS | CHLORFENVINPHOS | TRIAZOPHOS |
| METHYL-PARATHION | PHOSPHAMIDON | ENDOSULFAN |
| PARATHION | DICROTOPHOS | PROPAPHOS |
| FENITROTHION | MONOCROTOPHOS | SULPROFOS |
| CARBOFURAN | DICHLORVOS | PIRIMIPHOS-M |
| TRICHLORPHON | DIMETILAN | PHOSALONE |
| PHOXIM | DIAZINON | VAMIDOTHION |
| ACEPHATE | METHIDATION | CHLORMEPHOS |
| METAMIDOPHOS | JODFENPHOS | FORMOTHION |

-continued

| | | |
|---|---|---|
| ISAZOPHOS | DEMETON-S-METHYL | ETRIMIFOS |
| | | FONOFOS |

Suitable pyrethroids are, for example:

| | |
|---|---|
| BIORESMETHRIN | FENPROPATHRIN |
| CYPERMETHRIN | RESMETHRIN |
| CYHALOTHRIN | PHENOTHRIN |
| TEFLUTHRIN | FENVALERATE |
| PERMETHRIN | FENPROPATHRIN |
| DECAMETHRIN | FLUVALINATE |
| TRALOCYTRIN | |

Suitable insect-growth regulators that are used especially for controlling larval stages are, for example:
CHLORDIMEFORM
CYROMAZINE
CHLORFLUAZURON
BUPROFEZINE
DIFLUBENZURON
FLUFENOXURON The follow acaricides, for example, are suitable in accordance with the invention for controlling representatives of the order Acarina:
CHLORBENZILAT
CHLORPROPHYLAT
BROMPROPHYLAT
AMITRAZ
HEXYTHIAZOX
ROTENON
DIPEL The pesticidally active compound can be omitted from certain forms of the compositions of the invention. This is the case, for example, when extremely small larvae are to be attracted which become stuck to the matrix and therefore die without pesticidally active compound.

It is an essential feature of the present invention that the matrix of the compositions of the invention, in which the biologically active components are contained preferably in dissolved or emulsified form, consists for the most part of a liquid UV absorbent that is known per se. Liquid or flowable UV absorbers having an absorption range of from 270 to 400 nm have proved to be especially suitable for the purposes of the invention because on the one hand they ensure the necessary protection of the biological components contained in the composition against the influences of weather and light, and because on the other hand they have properties of permanent flowability. Consequently it is possible to impart to the compositions, if appropriate with the addition of certain viscosity-regulating substances, a consistency that makes them suitable for distribution in the form of droplets or droplet-like units or spots on a substrate, the substrate preferably being the leaves or other parts of the plants to be protected. These droplets, or droplet-like units or spots, which are each of an order of magnitude of from 1 to 100 $\mu$l, preferably from 5 to 40 $\mu$l, adhere to the relevant substrate and provide slow and controlled release over a prolonged time period of the substance that modifies the behaviour of the pests. On account of their differing biological, mobility and feeding behaviour, larval and adult stages of the pest are expediently controlled by producing droplets or droplet-like units of differing size on the attacked crop surfaces, these sizes preferably being from 1 to 20 $\mu$l for larvae and from 30 to 100 $\mu$l for adults. Generally, the slow or controlled release of the behaviour-modifying substance takes place over a period of up to 15 weeks, but at least up to 6 weeks. When the attracted pests come into contact with the permanently flowable or viscous composition, they inevitably take up from the surface thereof a pesticidally effective amount of the insecticide or acaricide contained in the composition. Such a controlled pesticide intake ("attract-and-kill" effect) is not provided, for example, by compostions that adhere to substrates, for example to parts of plants, in the form of a lacquer-like layer or in the form of solid and hard polymers.

For the compositions of the invention, there are used as a matrix base, that is to say as chief quantitative component of the matrix, liquid or flowable UV absorbers that are known per se, preferably having an absorption range of from 270 to 400 nm. Generally from 51 to 98% by weight, preferably from 70 to 98% by weight, of the compositions of the invention consists of the matrix, that is to say the UV absorber. It has proved advantageous for the UV absorbers themselves to a have a viscosity of from 1000 to 40,000 cp. Classes and types of UV absorbers that are suitable in accordance with the invention include, for example, the following, provided they are liquid and meet the other conditions of the invention:

1. 2-(2-hydroxyphenyl)-benzotriazoles

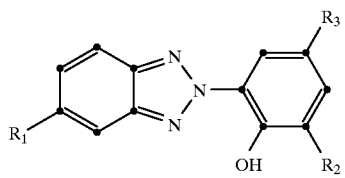

$R_1$=H, Cl;
$R_2$=H, alkyl, phenylalkyl, phenyl;
$R_3$=alkyl, phenylalkyl, phenyl, —$(CH_2)_2$—COO-alkyl.
The following UV absorbers of that type are preferred:

2. 2-hydroxy-4-alkoxybenzophenones

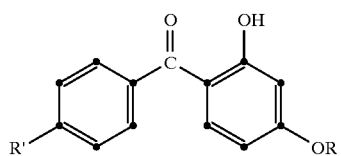

R=alkyl (e.g. iso-$C_8H_{17}$, —$C_{12}H_{25}$)

R'=H, alkyl, alkoxy

3. Oxalanilides

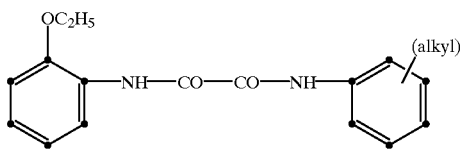

4. Cinnamic acid derivatives

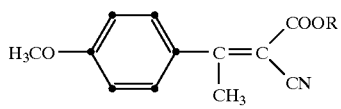

| Trade name | R$^1$ | R$^2$ | R$^3$ |
|---|---|---|---|
| Tinuvin 109 | Cl | —C(CH$_3$)$_3$ | 50% —CH$_2$—CH$_2$—C(=O)—O—C$_8$H$_{17}$ |
| | | | 50% —CH$_2$—CH$_2$—C(=O)—O—CH$_2$—CH(C$_2$H$_5$)—C$_4$H$_9$ |
| Tinuvin 171 | H | —C$_{12}$H$_{25}$-(isomeric mixture) | —CH$_3$ or C$_2$—C$_{12}$alkyl |
| Tinuvin 1130 | H | —C(CH$_3$)$_3$ | ca. 50% —CH$_2$—CH$_2$—C(=O)—O—(CH$_2$—CH$_2$—O)$_{300}$—H |
| | | | ca. 38% —[CH$_2$—CH$_2$—C(=O)—O—(CH$_2$—CH$_2$—O)$_{150}$—]$_2$ |
| | | | ca. 12% polyethyleneglycol (EO 300) |
| "SL 874" | H | —C(CH$_3$)$_3$ | —CH$_2$—CH$_2$—C(=O)—O—(CH$_2$)$_8$CH=CH—(CH$_2$)$_7$CH$_3$ |

R=alkyl (e.g. n-$C_4H_9$)

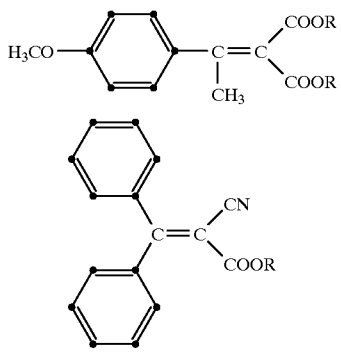

R=alkyl (e.g. $C_4H_9$,

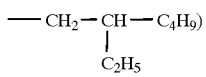

5. Triazine derivatives

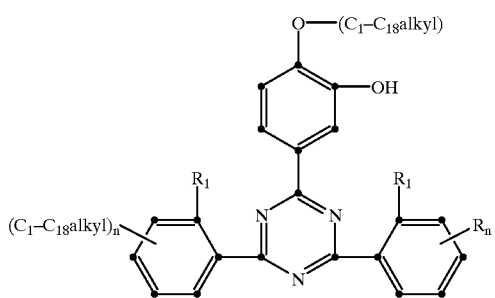

R=$C_1$–$C_{18}$alkyl, —O—($C_1$–$C_{18}$alkyl)
$R_1$=H, OH
n=0, 1 or 2

If necessary, the flowable preparations of the invention may contain conventional viscosity-regulating thickeners in an amount of from 1 to 47%, preferably from 1 to 20%, based on the weight of the matrix. The following, for example, are suitable as organic thickeners: acrylic acid polymers of high molecular weight and relatively high viscosity neutralised with bases ("Carbpole" types), polyvinylpyrrolidones, cellulose gums, especially cellulose alkyl esters and alkyl ethers ("Blanose" types), liquid polyalkylene glycol block mixed polymers of ethylene oxide and propylene oxide ("Pluronic" types) and also polyethylene glycols having a molecular weight of more than 10,000. Of the inorganic thickeners, the following, for example, may be mentioned: precipitated or pyrogenic silicic acids, aluminium oxides and natural mineral fillers, especially calcite, types of talcum, kaolins, bentonites, montmorillonites, smectites and attapulgite, aluminium oxide/silicon dioxide ("Aerosil" types) and sodium-aluminium silicates. Quartz sand or solid crosslinked polymers in powder form may be incorporated in the preparations as additional fillers.

In order to adjust the viscosity of the flowable preparations of the invention, it may be expedient in certain cases to add an inert solvent or diluent. These solvents should be compatible with the other constituents of the preparation and should preferably not be excessively volatile. The following solvents, for example, are suitable: ethers and ethereal compounds that are not readily volatile, such as dipropyl ether, dibutyl ether, dioxane, dimethoxyethane and tetrahydrofuran; N,N-di-alkylated carboxylic acid amides; aliphatic, aromatic and halogenated hydrocarbons, especially pentanes, hexanes, heptanes, octanes, hexadecane, toluene, xylenes, chlorohydrocarbons and chlorobenzenes, alcohols, such as ethanol, propanols, t-butanol and higher alcohols; nitriles, such as acetonitrile or propionitrile; and also ketones, for example methyl isopropyl ketone and methyl isobutyl ketone; alkyl esters of aliphatic carboxylic acids, such as propionic acid butyl ester, oxalic acid methyl ester, sebacic acid dibutyl ester and sebacic acid di-(2-ethylhexyl) ester. In general, only relatively small amounts of solvent, for example from 1 to 2% by weight, are contained in the formulations of the invention.

If necessary, the compositions of the invention may contain further formulation auxiliaries, which are used to adapt the compositions to specific conditions or to protect the biological active ingredients contained therein against particular environmental conditions and influences. Such formulation auxiliaries may be substances that ensure an additional UV protection, such as fine-particled carbon powder (e.g. carbon black), dyestuffs and colouring pigments (e.g. Sudan black, chromophthalic blue, Terasil blue, Cibacet yellow, titanium dioxide, zinc sulfate and zinc oxides), optical brighteners (e.g. Uvitex or Tinopal DMS), antioxidants (e.g. Tinuvin 765, butylhydroxytoluene or 2,6-di-tert-butyl-p-cresol) and in some cases also certain surface-active substances and emulsifiers (e.g. anionic surfactants: Na lauryl sulfate, dodecylbenzenesulfonic acid Ca salt, and non-ionic surfactants: fatty alcohol ethoxylates, alkylphenol ethoxylates, oleyl alcohol ethoxylates, ethylene oxide/propylene oxide block copolymers, fatty amine ethoxylates, silicone surfactants). Lime pigments and colouring pigments may be present in the compositions of the invention in an amount of from 1 to 20% by weight, preferably from 3 to 10% by weight, optical brighteners in an amount of from 0.1 to 2% by weight, antioxidants in an amount of from 0.1 to 5% by weight and surface-active substances and emulsifiers in an amount of from 0.1 to 1% by weight.

Within the scope of the method of the invention for the control of plant-destructive insects and representatives of the order Acarina, the compositions of the invention can be distributed in the form of droplets or droplet-like units or spots over the agricultural crop area to be treated using conventional devices as known to the person skilled in the art. Automatic pipettes with appropriate metering means, for example, have proved suitable for smaller areas. Also suitable are arrangements with intermittent production of droplets controlled mechanically or by compressed air, which are suitable mainly for extensive surface areas. Within the scope of the method of the invention, the number of droplets or droplet-like units or spots distributed over the crop area to be treated may vary in accordance with the nature of the pests to be controlled and their stages of development. From 50 to 100,000,000 of said droplets or droplet-like units or spots may be distributed per 1000 $m^2$ of crop area to be protected, from 50 to 1000 droplets or droplet-like units of the compositions of the invention generally being used to control adults and from 500,000 to 100,000,000 to control larvae.

The following Examples illustrate the invention, the percentage values in the formulations relating to weight unless otherwise indicated.

EXAMPLE 1

A flowable formulation having a viscosity of 25,000 cp is prepared by intimately mixing the following constituents:

| | |
|---|---|
| Tinuvin 171 (cf. above data) | 85.6% |
| carbon black powder (density 1.8–1.9 g/cm³, particle size 20 nm, surface area 240 m²/g) | 4.3% |
| Aerosil COK 84 (finely particulate SiO₂/Al₂O₃-84:16 % by wt.) | 2.6% |
| Furathiocarb | 4.3% |
| Codlemon | 0.1% |
| hexane | 3.1% |

Droplets of this formulation, each of 100 μl, are applied to an aluminium sheet and each day are exposed alternately to UV radiation (UV lamp) at 35° C. for 9 hours and to a temperature of 12° C. in darkness for 15 hours. Droplets with different durations of treatment are then, immediately after that treatment, examined in a "wind tunnel" for insecticidal activity and their ability to attract *Cydia pomonella* males.

The wind tunnel used, as has already been described in principle in the literature (cf. J. R. Hiller and W. L. Roelofs, J. Chem. Ecology, 4, 187–198, 1978), consists essentially of a sealed tunnel of transparent material of rectangular cross-section. A droplet of the attractant/insecticide formulation as described above is arranged at one end of the tunnel. Short open glass tubes for receiving the insects (*Cydia pomonella* males) and a take-off pad are arranged at the opposite end of the tunnel. An attracting effect of the attractant contained in the droplet, which takes effect on the insect in the glass tube when a stream of air is produced, causes a state of excitation in the *Cydia pomonella* males, which is manifested initially by motorisation and buzzing of the moths' wings. The source of attractant (that is the droplet containing the active ingredient) is then specifically flown to from the take-off pad. In the case of substances that do not have an attracting effect, the moth remains, unstimulated, in the open glass tube. The glass tube is occupied by one moth for every flight test. On average, 40 flight tests are carried out for each formulation to be tested. For the purposes of evaluation, the percentage of moths that fly in the direction of the droplet and touch ("contact") it is ascertained. The moths that touch the droplets are captured and their percentage mortality is ascertained after 24 hours. The results obtained, compared with control batches without attractant, are compiled in the following Table:

| Action on | Duration of treatment of the droplets (in days) | | | | |
|---|---|---|---|---|---|
| C. pomonella | 0 | 3 | 7 | 14 | 21 |
| % contact | 95 | 85 | 95 | 95 | 80 |
| % mortality | 100 | 100 | 100 | 100 | 100 |

EXAMPLE 2

A formulation having a viscosity of 20,000 cp is prepared from the following constituents in accordance with the preceding Example 1:

| | |
|---|---|
| Tinuvin 171 | 85.5% |
| carbon black powder (particle size 35 nm, surface area 1000 m²/g) | 4.3% |
| Sudan black B (dyestuff) | 4.3% |
| Furathiocarb | 4.3% |
| Codlemon | 0.2% |
| hexane | 1.4% |

Droplets of 100 μl of this formulation are applied in the field to the leaves of apple trees and tested in the wind tunnel after 35 days. These droplets still exhibit a very good attracting effect and insecticidal activity in the wind tunnel. 80% of the tested males of *Cydia pomonella* are attracted by such a droplet, fly to it and touch it. After 24 hours the mortality of these males is 100%. The wind tunnel tests are carried out as indicated in Example 1.

EXAMPLE 3

A formulation having a viscosity of 20,000 cp is prepared from the following constituents in accordance with the above Example 1:

| | |
|---|---|
| Tinuvin 171 | 81.5% |
| Aerosil COK 84 | 3.2% |
| carbon black powder | 4.1% |
| Sudan black B | 4.1% |
| Furathiocarb | 4.1% |
| Codlemon | 0.1% |
| hexane | 2.9% |

In a field test with the codling moth *Cydia pomonella*, a 1.2 ha orchard with about 1200 apple trees is treated with 8 droplets, each of 100 μl, of the above flowable formulation per tree (approximately 8000 droplets/ha). A second corresponding application with this formulation is carried out 41 days later. Figures for the attack in the treated orchard compared with an untreated control orchard are as follows:

| Evaluation point of time (No. of days after first application) | % attack by C. pomonella | |
|---|---|---|
| | treated | untreated |
| 46 | 0.6% | 7% |
| 87 | 0.8% | 22% |

EXAMPLE 4

A viscous formulation is prepared from the following constituents in accordance with the above Example 1:

| | | |
|---|---|---|
| Tinuvin 171 | | 80.1% |
| Tinuvin 765 | | 1.6% |
| Aerosil COK 84 | | 3.2% |
| carbon powder (particle size 20 nm) | | 4.0% |
| Sudan black B | | 4.0% |
| METHIDATHION | | 4.0% |
| 29-dodecenyl acetate | | 0.05% |
| dodecanyl acetate | (pheromone mixture) | 0.05% |
| octadecanyl acetate | | 0.1% |
| hexane | | 2.9% |

The prepared formulation is tested in a wind tunnel against *Eupoecilia ambiguella* males in accordance with the method described in Example 1. With droplets of the above formulation that had been treated for 7 days in the manner described in Example 1, evaluation indicated a mortality of from 75 to 100%.

EXAMPLE 5

A formulation having a viscosity of 20,000 cp is prepared from the following constituents in accordance with the above Example 1:

| | |
|---|---|
| Tinuvin 171 | 81.2% |
| Aerosil COK 84 | 3.2% |
| carbon black powder | 4.0% |
| Sudan black B | 4.0% |
| Furathiocarb | 4.5% |
| hexane | 3.0% |
| pheromone | 0.1% |

Composition of the pheromone used: Proportions by weight:

| | |
|---|---|
| (Z)9-tetradecenyl acetate | 9 |
| (Z)11-tetradecanyl acetate | 1 |
| (Z)9-tetradecenol | 1 |
| (Z)11-tetradecenol | 0.2 |

In a field test with the moth *Adoxophyes reticulana*, 1 droplet of 100 µl of the formulation is placed in the middle of a paper sheet 16×16 cm coated with glue (polybutylene). The paper is secured around an approximately 5 cm thick branch of an apple tree about 2 m above the ground and the moths that have been attracted by the formulation droplet and caught on the sticky paper are counted weekly. A rubber stopper treated with the same amount of pheromone, which is also secured to the middle of a sticky paper, is used as a control. 6 replicates were carried out per variant:

| Evaluation point of time | Number of moths caught (period of capture 1 week, 6 traps) | |
|---|---|---|
| (No. of days after application) | formulation | rubber stopper (control) |
| 14 | 67 | 7 |
| 70 | 17 | 6 |

EXAMPLE 6

A formulation having a viscosity of 20,000 cp is prepared from the following constituents in accordance with the above Example 1:

| | |
|---|---|
| Tinuvin 171 | 81.2% |
| Aerosil COK 84 | 3.2% |
| carbon black powder | 4.0% |
| Sudan black B | 4.0% |
| Furathiocarb | 4.5% |
| hexane | 3.0% |
| pheromone | 0.1% |

Composition of the pheromone used: Proportions by weight:

| | |
|---|---|
| (Z)9-dodecenyl acetate | 1 |
| dodecanyl acetate | 1 |
| octadecanyl acetate | 2 |

In a field test with the vine moth *Eupoecilia ambiguella* 1 droplet of 100 µl is placed in the middle of a paper sheet 16×16 cm coated with glue (polybutylene). The paper is secured around a vine at eye level, and the moths that have been attracted by the formulation droplet and caught on the sticky paper are counted weekly. A rubber stopper treated with the same amount of pheromone, which is also secured to the middle of a sticky paper, is used as a control. 6 replicates were carried out per variant:

| Evaluation point of time | Number of moths caught (period of capture 1 week, 6 traps) | |
|---|---|---|
| (No. of days after application) | formulation | rubber peg (control) |
| 14 | 19 | 17 |

EXAMPLE 7

A formulation having a viscosity of 20,000 cp is prepared from the following constituents in accordance with the above Example 1:

| | |
|---|---|
| Tinuvin 171 | 83.6% |
| Aerosil COK 84 | 3.3% |
| carbon black powder | 4.2% |
| Sudan black B | 4.2% |
| Deltamethrin | 4.2% |
| hexane | 0.4% |
| pheromone | 0.2% |

Composition of the pheromone used: Proportions by weight:

| | |
|---|---|
| Z,Z-7,11-hexadecadienyl acetate | 1 |
| Z,E-7,11-hexadecadienyl acetate | 1 |

In a field test with the Pink Bollworm (*Pectinophora gossypiella*), an area of 0.75 ha of cotton is treated with droplets, each of 50 $\mu$l of the above formulation (approximately 10,000 droplets/ha). The action is ascertained as a percentage of the capsules attacked by larvae. Figures for the attack of the treated plot compared with an untreated control plot are as follows:

| Evaluation point of time (No. of days | % attack by *P. gossypiella* | |
|---|---|---|
| after application) | treated | untreated (control) |
| 30 | 0.14% | 3.3% |

EXAMPLE 8

A formulation having a viscosity of 20,000 cp is prepared from the following constituents in accordance with the above Example 1:

| | |
|---|---|
| Tinuvin 171 | 85.4% |
| Aerosil COK 84 | 3.4% |
| carbon black powder | 4.3% |
| Sudan black B | 4.3% |
| Deltamethrin | 0.9% |

-continued

| | |
|---|---|
| hexane | 1.5% |
| pheromone | 0.2% |

Composition of the pheromone used: Proportions by weight:

| | |
|---|---|
| (+)cis-2-isopropenyl-1-methylcyclobutane ethanol | 40 |
| (Z)-3,3-dimethyl-Δ-1,β-cyclohexane ethanol | 30 |
| (Z)-3,3-dimethyl-Δ-1,α-cyclohexane acetaldehyde | 15 |
| (E)-3,3-dimethyl-Δ-1,α-cyclohexane acetaldehyde | 15 |

Droplets each of 100 μl are placed on an aluminium sheet and exposed under a UV lamp for 3 days. Adult *Anthonomus grandis* are then brought into contact with the formulation for a short period, and the mortality is observed after 24 hours.

An analogous formulation without Deltamethrin is used as a control.

| Exposure of the formulation | % mortality of *A. grandis* 24 hours after exposure | |
|---|---|---|
| (No. of days under UV) | treated | untreated (control) |
| 3 | 100% | 5% |

EXAMPLE 9

A formulation having a viscosity of 20,000 cp is prepared from the following constituents in accordance with the above Example 1:

| | |
|---|---|
| Tinuvin 171 | 83.7% |
| Aerosil COK 84 | 3.4% |
| carbon black powder | 4.3% |
| Sudan black B | 4.3% |
| Methidathion | 2.7% |
| hexane | 1.5% |
| 8-methyl-2-decanol propanoate (pheromone) | 0.1% |

Droplets each of 100 μl are placed on an aluminium sheet and exposed under a UV lamp for 5 days. Adult *Diabrotica balteata* are then brought into contact with the formulation for a short period, and the mortality is observed after 24 hours.

An analogous formulation without Methidathion is used as a control.

| Exposure of the formulation | % mortality of *D. balteata* 24 hours after exposure | |
|---|---|---|
| (No. of days under UV) | treated | untreated (control) |
| 5 | 100% | 0% |

EXAMPLE 10

A formulation having a viscosity of 20,000 cp is prepared from the following constituents in accordance with the above Example 1:

| | |
|---|---|
| Tinuvin 171 | 85.4% |
| Aerosil COK 84 | 3.4% |
| carbon black powder | 4.3% |
| Sudan black B | 4.3% |
| Cypermethrin | 0.9% |
| hexane | 1.5% |
| estragol | 0.1% |
| 4-methoxycinnamaldehyde (pheromone) | 0.1% |

Droplets each of 100 μl are placed on an aluminium sheet and exposed under a UV lamp for 4 days. In each case one leg of an adult *Diabrotica balteata* is then brought into contact with the formulation for a short period, and the mortality is observed after 24 hours. An analogous formulation without Cypermethrin is used as a control.

| Exposure of the formulation | % mortality of *D. balteata* 24 hours after exposure | |
|---|---|---|
| (No. of days under UV) | treated | untreated (control) |
| 4 | 100% | 0% |

EXAMPLE 11

A formulation having a viscosity of 20,000 cp is prepared from the following constituents in accordance with the above Example 1:

| | |
|---|---|
| Tinuvin 171 | 27.2% |
| quartz sand (particle size < 0.7 mm) | 66.6% |
| Aerosil COK 84 | 1.1% |
| carbon black powder | 1.4% |
| Sudan black B | 1.4% |
| Furathiocarb | 1.4% |
| hexane | 0.9% |
| E,E-8,10-dodecadienol (pheromone) | 0.03% |

Droplets each of 100 μl are placed on an aluminium sheet, exposed under a UV lamp for 49 days and then tested in the wind tunnel. These droplets still exhibit a very good attracting effect and insecticidal activity in the wind tunnel. 100% of the tested males of *Cydia pomonella* are attracted by such a droplet, fly to it and touch it. After 24 hours the mortality of these males is 100%. The wind tunnel tests are carried out as indicated in Example 1.

EXAMPLES 12 to 20

The following formulations are prepared as described in Example 1, and tested against *Cydia pomonella* according to the methods described in Examples 1 to 3, mortality rates of from 75 to 100% being achieved:

EXAMPLE

| Example No. | | |
|---|---|---|
| 12 | Tinuvin 171 (see above data) | 90.2% |
| | Aerosil COK 84 | 4.1% |
| | Furathiocarb | 4.5% |
| | Codlemon | 0.1% |
| | sebacic acid dibutyl ester | 1.1% |
| 13 | Tinuvin 1130 (see above data) | 84.9% |

-continued

| Example No. | | |
|---|---|---|
| | Aerosil COK 84 | 4.2% |
| | carbon powder | 4.2% |
| | Furathiocarb | 4.2% |
| | Codlemon | 0.1% |
| | ethanol | 2.4% |
| 14 | Tinuvin 1130 | 80.9% |
| | Aerosil COK 84 | 3.6% |
| | carbon powder | 4.0% |
| | Sudan black B | 4.0% |
| | Furathiocarb | 4.0% |
| | Codlemon | 0.1% |
| | ethanol | 3.4% |
| 15 | Tinuvin 171 | 81.0% |
| | Aerosil COK 84 | 4.0% |
| | carbon black (particle size 13 nm) | 4.0% |
| | Sudan black B | 4.0% |
| | Furathiocarb | 4.0% |
| | Codlemon | 0.1% |
| | sebacic acid dibutyl ester | 2.9% |
| 16 | Tinuvin 171 | 84.9% |
| | Aerosil COK 84 | 3.4% |
| | Furathiocarb | 4.3% |
| | Cibacetyellow 2CG (dyestuff) | 4.3% |
| | Codlemon | 0.1% |
| | sebacic acid dibutyl ester | 3.0% |
| 17 | Tinuvin 171 | 89.7% |
| | Aerosil COK 84 | 4.0% |
| | Furathiocarb | 4.0% |
| | Erythrosin (dyestuff) | 1.0% |
| | Codlemon | 0.1% |
| | hexane | 1.2% |
| 18 | Tinuvin 171 | 80.2% |
| | Tinuvin 765 | 1.6% |
| | Aerosil COK 84 | 3.2% |
| | carbon powder (particle size 20 nm) | 4.0% |
| | Sudan black B | 4.0% |
| | Furathiocarb | 4.0% |
| | Codlemon | 0.1% |
| | hexane | 3.9% |
| 19 | Tinuvin 109 | 80.2% |
| | Tinuvin 765 | 1.6% |
| | Aerosil COK 84 | 3.2% |
| | carbon powder (particle size 20 nm) | 4.0% |
| | Sudan black B (dyestuff) | 4.0% |
| | Furathiocarb | 4.0% |
| | Codlemon | 0.1% |
| | hexane | 2.9% |
| 20 | Tinuvin 171 | 61.0% |
| | Aerosil COK 84 | 10.0% |
| | Furathiocarb | 4.5% |
| | Codlemon | 4.5% |
| | hexane | 10.0% |

What is claimed is:

1. A viscous, non-hardening composition that is resistant to water and weather for controlling harmful pests selected from the group consisting of insects and representatives of the order Acarina, which composition comprises:

a) about 0.01–30% by weight of a pheromone or kairomone;

b) about 0.1–10% of a pesticidal compound that is compatible with other constituents of said composition; and c) about 51–98% of an ultraviolet-absorber having and absorption range of from 270 to 400 nm selected from the group consisting of 2-H-benzotriazoles, 2-hydroxyalkoxybenzophenones, oxalanilides, cinnamic acid esters and triazines;

wherein the pheromone or kairomone is slowly released in a biologically effective amount over a period of time; and wherein said composition has a viscosity of at least about 20,000 cp and is distributable for direct application without dilution as droplets or spots.

2. The composition of claim 1, further including a viscosity-regulating thickener or solvent, an antioxidant, a dyestuff or coloring pigment, an optical brightener, a tackifier, or a surface-active substance.

3. The composition of claim 1, wherein the composition contains about 1–47% by weight of a viscosity-regulating thickener or solvent.

4. The composition of claim 1, further including finely particulate carbon as an additional UV absorber.

5. The composition of claim 1, wherein the pheromone or kairomone is in microencapsulated form having controlled release properties.

6. The composition of claim 1, wherein the ultraviolet-absorber is a 2-H-benzotriazole.

7. The composition of claim 1, wherein the pheromone or kairomone is a pheromone which is about 0.01 to 2.0% by weight of the composition.

8. The composition of claim 7, wherein the pheromone is Codlemon.

* * * * *